US012175662B2

(12) United States Patent
Alizad et al.

(10) Patent No.: US 12,175,662 B2
(45) Date of Patent: Dec. 24, 2024

(54) METHODS FOR EXTRACTING AND QUANTIFYING DIAGNOSTIC BIOMARKERS FROM ULTRASOUND MICROVESSEL IMAGES

(71) Applicant: Mayo Foundation for Medical Education and Research, Rochester, MN (US)

(72) Inventors: Azra Alizad, Rochester, MN (US); Mostafa Fatemi, Rochester, MN (US); Redouane Ternifi, Rochester, MN (US); Yinong Wang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 490 days.

(21) Appl. No.: 17/466,773

(22) Filed: Sep. 3, 2021

(65) Prior Publication Data

US 2022/0067933 A1    Mar. 3, 2022

Related U.S. Application Data

(60) Provisional application No. 63/074,085, filed on Sep. 3, 2020.

(51) Int. Cl.
| | |
|---|---|
| *G06T 7/00* | (2017.01) |
| *G06T 7/155* | (2017.01) |
| *G06T 7/73* | (2017.01) |
| *G16H 50/20* | (2018.01) |
| *G16H 50/30* | (2018.01) |

(52) U.S. Cl.
CPC .......... *G06T 7/0012* (2013.01); *G06T 7/155* (2017.01); *G06T 7/73* (2017.01); *G16H 50/20* (2018.01); *G16H 50/30* (2018.01); *G06T 2207/10132* (2013.01); *G06T 2207/20024* (2013.01); *G06T 2207/30068* (2013.01); (Continued)

(58) Field of Classification Search
None
See application file for complete search history.

(56) References Cited

U.S. PATENT DOCUMENTS

| | | | | |
|---|---|---|---|---|
| 2020/0305840 A1* | 10/2020 | Sboros | ................. | A61B 8/5207 |
| 2022/0028067 A1* | 1/2022 | Alizad | ...................... | G06T 7/11 |
| 2022/0087651 A1* | 3/2022 | Alizad | ................. | A61B 8/5207 |

OTHER PUBLICATIONS

Bullit, E., et al., "Vessel Tortuosity and Brain Tumor Malignancy: A Blinded Study" Acad Radiol (2005) 12:1232-1240.
(Continued)

*Primary Examiner* — Leon Flores
(74) *Attorney, Agent, or Firm* — Quarles & Brady LLP

(57) ABSTRACT

The present disclosure addresses a quantitative analysis of tumor vascularity patterns, with the goal of identifying biomarkers correlated with malignancy. Herein, we identify new types of quantitative ultrasound biomarkers of microvessel morphology that correlate with the state of the disease in question. We propose a novel method to automatically extract quantitative features related to the morphology and distribution of the vascular networks reconstructed from contrast-free ultrasound data. For instance, spatial vascularity pattern, bifurcation angle, Murray's deviation, fractal dimension and closet vessel distance were clearly depicted.

26 Claims, 12 Drawing Sheets

(52) U.S. Cl.
CPC ............... *G06T 2207/30096* (2013.01); *G06T 2207/30101* (2013.01); *G06T 2207/30172* (2013.01)

(56) References Cited

OTHER PUBLICATIONS

Gessner, R.C., et al., "Mapping Microvasculature with Acoustic Angiography Yields Quantifiable Differences between Healthy and Tumor-bearing Tissue vols. in a Rodent Model" Radiology (2012) vol. 264: No. 3 pp. 733-740.

Gruber, I.V., et al., "Measurement of tumour size with mammography, sonography and magnetic resonance imaging as compared to histological tumour size in primary breast cancer" BMC Cancer (2013) 13:328.

Gong, P., et al., "Ultrasensitive Ultrasound Microvessel Imaging for Characterizing Benign and Malignant Breast Tumors" Ultrasound in Med. & Biol. (2019) vol. 45, No. 12, pp. 3128-3136.

Lam, L., et al., "Thinning Methodologies—A Comprehensive Survey" IEEE Trans. on Pattern Analysis and Machine Intelligence (1992) 14:869-885.

Li, C., et al., "In Vivo Breast Sound-Speed Imaging With Ultrasound Tomography" Ultrasound Med Biol. (2009) 35(10): 1615-1628.

Shelton, S.E., et al., "Quantification of Microvascular Tortuosity During Tumor Evolution Using Acoustic Angiography" Ultrasound in Med. & Biol. (2015) vol. 41, No. 7, pp. 1896-1904.

\* cited by examiner

METHODS FOR EXTRACTING AND QUANTIFYING DIAGNOSTIC BIOMARKERS FROM ULTRASOUND MICROVESSEL IMAGES

CROSS-REFERENCE TO RELATED APPLICATIONS

This application claims the benefit of U.S. Provisional Patent Application Ser. No. 63/074,085, filed on Sep. 3, 2020, and entitled "METHODS FOR EXTRACTING DIAGNOSTIC BIOMARKERS FROM ULTRASOUND MICROVESSEL IMAGES," which is herein incorporated by reference in its entirety.

STATEMENT REGARDING FEDERALLY SPONSORED RESEARCH

This invention was made with government support under CA239548 awarded by the National Institutes of Health. The government has certain rights in the invention.

BACKGROUND

Angiogenesis, the growth of new microvessels, plays an essential role in pathogenesis and outcome of the deadliest maladies of the modern world, such as cancers. Quantification of microvessel morphological features could play an important role in disease diagnosis and tumor classification. For example, malignant tumor vascularity is known to present heterogeneous organization, structurally abnormal and chaotic. It has also been shown that microvascular parameters such as tortuosity, vessel size and branching correlate well with tumor aggressiveness.

Microvasculature architecture is known to be associated with tissue state and pathology. Different conditions and diseases can alter vasculature at different size scales. For instance, malignant tumor growth has been found to coincide with changes in the vascularity of normal tissue; malignant tumors are known to present different mechanical features, leading to the growth of more permeable and tortuous vessels; and vessel tortuosity has been found to reveal information about some diseases. It has also been shown that microvascular parameters such as vessel size and branching correlate well with tumor aggressiveness and angiogenesis.

Quantitative information can be derived from microvessel images obtained by contrast agent ultrasound imaging. These techniques seek to screen a measure of blood flow inside a tissue volume by testing the increase in ultrasound signal from the blood pool contrast agents. While these methods have been shown to quantify the architecture of the blood vessels in thyroid nodules and breast lesions, the use of contrast agents remains a barrier for these methods finding routine clinical use.

It would be desirable, then, to provide methods for quantifying features of microvessel images obtained without the use of a contrast agent.

SUMMARY OF THE DISCLOSURE

The present disclosure addresses the aforementioned drawbacks by providing a method for generating quantitative vessel feature data from non-contrast ultrasound data. A microvessel image is provided to a computer system, where the microvessel image has been acquired with an ultrasound system from a subject without a contrast agent. The microvessel image is converted to a binary image using the computer system, where the binary image contains pixels with first binary values and pixels with second binary values, wherein pixels with the first binary value correspond to segmented vessels. Vessel segment data are generated from the binary image by morphologically filtering the binary image using the computer system, where the vessel segment data represent segmented vessels depicted in the microvessel image. Quantitative vessel feature data are generated based on at least one of the binary image and the vessel segment data. The quantitative vessel feature data include at least one of quantitative vessel structure data, quantitative vessel Murray's deviation data, quantitative bifurcation angle data, quantitative closest vessel distance data, quantitative fractal dimension data, and quantitative spatial vascularity pattern data. The quantitative vessel feature data can then be displayed to a user.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
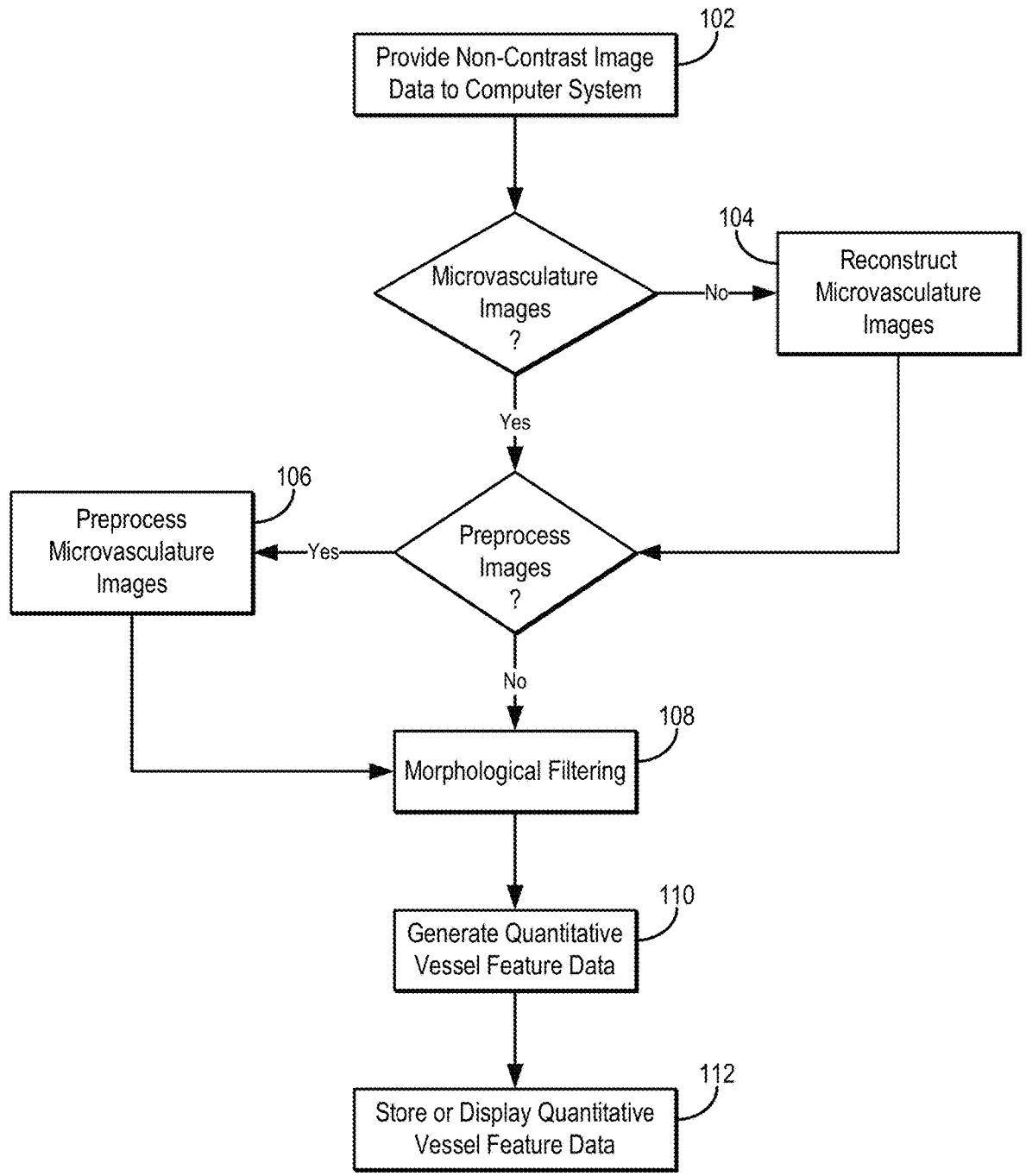
FIG. 1 is a flowchart setting forth the steps of an example method for generating quantitative vessel feature data from non-contrast ultrasound images of microvasculature.

Described here are systems and methods for quantifying vessel features in non-contrast microvessel images obtained with an ultrasound imaging system. Vessel features that are quantified include, but are not limited to, vessel morphology features such as spatial vascularity pattern, bifurcation angle, Murray's deviation, fractal dimension, and closet vessel distance.

Advantageously, the present disclosure describes systems and methods for generating quantitative ultrasound biomarkers of microvessel morphology that correlate with the state of a disease in question. As one example, quantitative features related to the morphology and distribution of the vascular networks can be automatically extracted, estimated, or otherwise derived from ultrasound microvessel images reconstructed from contrast-free ultrasound data.

The systems and methods described in the present disclosure may be used to analyze the structure of blood vessels and to extract quantitative features from ultrasound Doppler images (e.g., high-definition ultrasound Doppler images). These quantitative features can be used to characterize or differentiate various different vessel architectures and, therefore, to analyze the vascular network. Advantageously, the microvessel morphology parameters generated using the described methods enable visualization and analysis of higher structural complexity in vascular networks. This information may then be used by a clinician to aid a diagnosis of various different diseases. For instance, the systems and methods described in the present disclosure provide a tool for quantification of microvessel images from non-contrast ultrasound imaging, and may result in potential biomarkers for the diagnosis of some diseases, such as breast cancer.

Morphological features of small vessels provide useful information regarding underlying tissue, especially in cancerous tumors. The systems and methods described in the present disclosure provide for quantifying morphological features from microvessel images obtained by non-contrast ultrasound imaging.

Previous methods for quantitative analysis of ultrasound microvessel images don't allow for analysis of central and/or peripheral distributions of vasculature in a region-of-interest. Advantageously, the quantitative vessel spatial vascularity patter ("SVP") parameter described in the present disclosure enables the vessel density can be visualized or otherwise discerned ring-by-ring through the lesion size. With SVP classification, the lesion can be considered to have a perilesional vascularization or classified as intralesional vascularization, for example.

The fractal dimension ("FD") is a sensitive parameter to capture vascular complexity. It is contemplated that disorders in the tumor microvasculature system can be classified or otherwise assessed based on fractal analysis of ultrasound microvessel images, such as by computing FD from ultrasound microvessel images. For example, ultrasound microvessel FD can enable analysis of breast cancer vascular structure, and can advantageously be enable microvasculature characterization using FD based on non-contrast ultrasound imaging.

Additionally or alternatively, Murray's deviation and bifurcation angle can be used as quantitative parameters of ultrasound microvessel morphology in vascular characterization. The systems and methods described in the present disclosure allow for microvasculature characterization to be based on the quantitative analysis of these parameters from non-contrast ultrasound imaging data using, for example, an automated algorithm. For example, using this analysis, microvasculature network features such as sub-vessel diameters and the angle between the fitted daughter vessels can be analyzed.

Using the systems and methods described in the present disclosure, closet distance parameters in the microvasculature can also be computed from non-contrast ultrasound imaging data and used to classify vessels based on vessel diameter size, the distance between the center of each vessel segment, and the like.

Referring now to FIG. 1, a flowchart is illustrated as setting forth the steps of an example method for generating quantitative vessel feature data from non-contrast ultrasound data. The method includes providing image data to a computer system, as indicated at step 102. The image data may be provided to the computer system by retrieving or otherwise accessing image data from a memory or other data storage device or medium. Additionally or alternatively, the image data may be provided to the computer system by acquiring image data with an ultrasound imaging system and communicating the acquired image data to the computer system, which may form a part of the ultrasound imaging system. In any such instance, the image data are preferably acquired without the use of an ultrasound contrast agent (e.g., a microbubbles-based contrast agent). The image data may be two-dimensional image data or three-dimensional image data.

In some instances, the image data contain microvessel images that depict the microvasculature in a region of a subject from which the images were obtained. In other instances, the image data contain a sequence of ultrasound images, such as a sequence of plane wave ultrasound images. In these instances, one or more microvessel images are first reconstructed from the sequence of ultrasound images, as indicated at optional step 104.

As a non-limiting example, when the image data contain ultrasound plane wave image data, the data can be stored or otherwise converted into an in-phase-quadrature ("IQ") format. These data can be characterized by a complex-valued variable that is a function of the lateral dimension (x), axial dimension (z), and time (t) (i.e., ultrasound imaging slow time). For instance, the signal can be described as, $$s(x,z,t) = c(x,z,t) + b(x,z,t) + n(x,z,t) \quad (1);$$

Where $c(x,z,t)$ is the clutter signal, $b(x,z,t)$ is the blood signal, and $n(x,z,t)$ is additive thermal noise. Spatial and temporal characteristics of these three components differ. The additive thermal noise can be considered as zero Gaussian white noise. The signal corresponds to a signal data tensor, S, with dimensions $n_x \times n_z \times n_t$, where $n_x$ is the number of spatial samples along the x-direction (i.e., the lateral direction), $n_z$ is the number of spatial samples along the z-direction (i.e., the axial direction), and $n_t$ is the number of samples over time. The signal data tensor can be reshaped to form a Casorati matrix by transforming the tensor into a two-dimensional spatiotemporal matrix, $S_C$, with dimensions $(n_x n_z) \times n_t$.

Using a singular value decomposition ("SVD") of this spatiotemporal matrix results in, $$S_C = U \Delta V^\wedge \quad (2);$$

where $\Delta$ is an $(n_x \times n_z) \times n_t$ non-square diagonal matrix, U is an $(n_x \times n_z) \times (n_x \times n_z)$ matrix, V is an $n_t \times n_t$ matrix, and "\" indicates the conjugate transpose. The matrices U and V are orthonormal matrices, and the columns of these matrices correspond to the spatial and temporal singular vectors, respectively, of $S_C$.

The matrix, $S_C$, can be decomposed into a sum of rank one matrix, $$S_C = \sum_i \lambda_i A_i = \sum_i \lambda_i U_i \otimes V_i; \quad (3)$$

where $U_i$ and $V_i$ are the $i^{th}$ columns of U and V, respectively; $\lambda_i$ is the $i^{th}$ ordered singular value of $S_C$; and "$\otimes$" denotes the outer product operation. Each column $V_i$ is a temporal signal with length $n_t$ and each column $U_i$ is a spatial signal with dimensionality $n_x \times n_z$ (i.e., a two-dimensional spatial image, $I_i$); hence, $$s(x, z, t) = \sum_{i=1}^{rank(S_C)} \lambda_i I_i(x, z) V_i(t). \quad (4)$$

In a low rank clutter filtering framework, the tissue component can be considered to correspond to the first few dominant singular values and vectors, while the blood signal can be formed by the subsequent singular values when sorted in a descending order. Based on these assumptions on tissue and blood signals, clutter removal is performed using a threshold, n, on the number of singular vectors removed from s(x, z, t). Therefore, the blood signal can be derived as follows, $$s_{blood}(x, z, t) = s(x, z, t) - \sum_{i=1}^{n} \lambda_i I_i(x, z) V_i(t). \quad (5)$$

The threshold, n, can be selected based on setting a threshold on the slope of the second order derivative of the eigenvalues decay. The filtered blood signal, $S_{blood}$ (x, Z, t), can be used to produce a power Doppler image as, $$I(x, z) = \sum_{k=1}^{K} |s_{blood}(x, z, kT)|^2; \quad (6)$$

where T is the sampling time between two successive ultrasound frames, which may be successive ultrafast ultrasound frames. The clutter removal performance can be further enhanced by enforcing a unilateral Doppler shift, which is expected to occur from the unidirectional flow in vessels, before forming the intensity image in Eqn. (6). In these instances, the final image can be formed as, $$I(x,z)=|I_p-I_n| \quad (7);$$

where $I_P$ is the energy at the positive frequency side of the spectrum, $$I_p = \int_0^\infty |S_{blood}(x, z, f)|^2 df; \quad (8)$$

where $S_{blood}(x, z, f)$ is the Fourier transform of the blood signal, $S_{blood}(x, z, t)$, and $I_n$ is the energy at the negative frequency side of the spectrum, $$I_n = \int_{-\infty}^{0} |S_{blood}(x, z, f)|^2 df. \quad (9)$$

The image, I(x, z) can be filtered to remove background noise. As one example, the image can be filtered using a top hat filter ("THF"). A THF implements a background estimation followed by a background subtraction operation. The output image of the THF can be denoted as $I_T(x, z)$.

The microvessel images are then preprocessed, as generally indicated at step 106. In some instances, the microvessel images may have already been preprocessed (e.g., the microvessel images stored in the memory or other data storage device or medium are preprocessed microvessel images), in which case step 106 can be skipped. In general, preprocessing the microvessel images can include vessel filtering to enhance the structure of vessels depicted in the microvessel images, and to provide adequate background separation for segmentation.

As one example of preprocessing a microvessel image, to enhance the visibility of the microvessel image in the presence of strong background signals, morphological filtering based on a THF can be used. Due to background noise, however, random patterns may also be present at the output of a THF. Hence, in some implementations, vessel enhancement filters can be used to penalize background noise and further enhance vessel structure. Enhancement filters based on the analysis of eigenvalues of a Hessian matrix applied on a two-dimensional image selectively amplify a specific local intensity profile or structure in an image. Hessian-based filters distinguish between different local structures by analyzing the second order intensity derivatives at each point in the image. To enhance the local structures of various sizes, the analysis is typically performed on a Gaussian scale space of the image.

Figure 2:
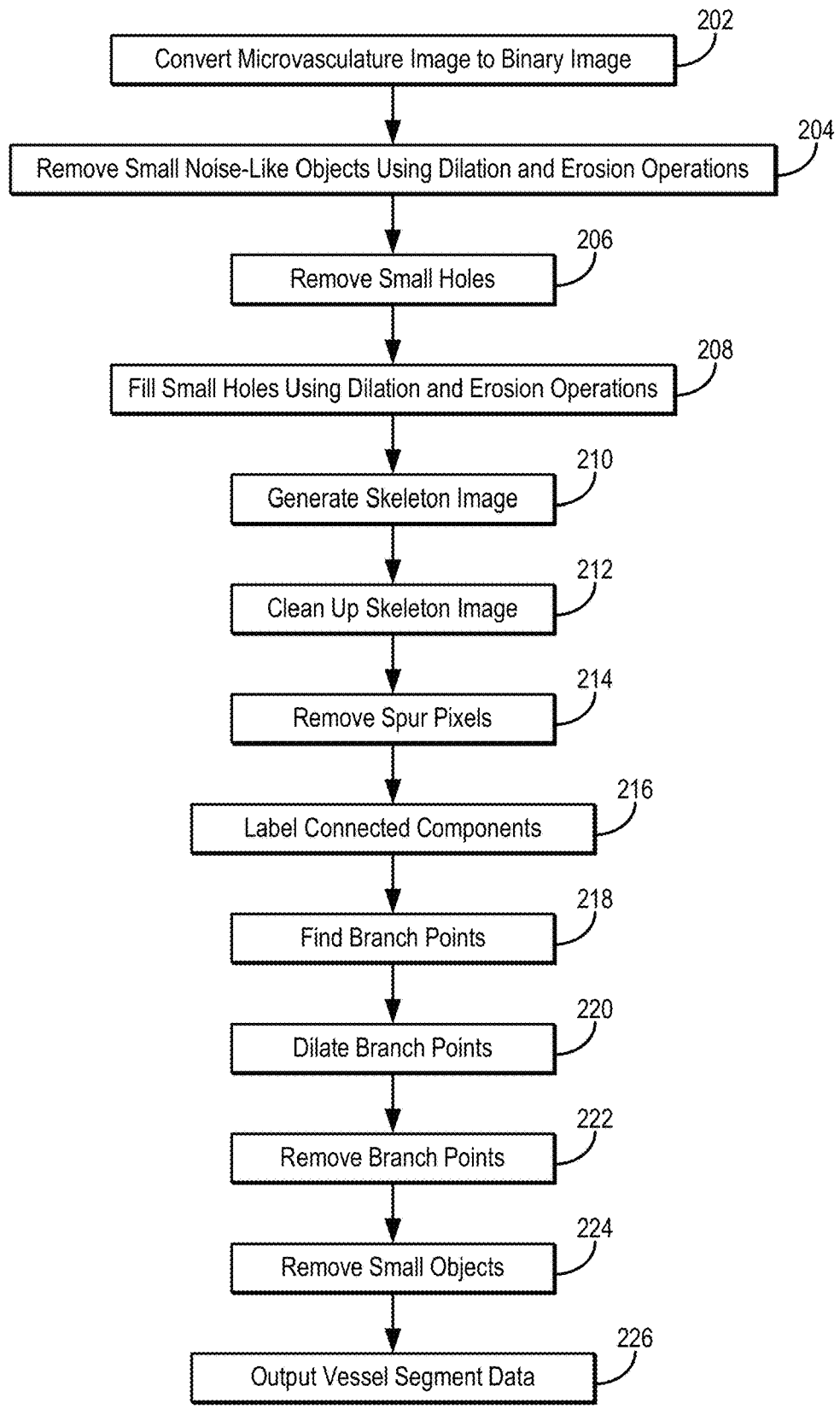
FIG. 2 is a flowchart setting forth examples of morphological filtering that can be implemented to generate vessel segment data.

The preprocessed microvessel images are next filtered with one or more morphological filters, as indicated at step 108. An example of morphological filtering that can be applied to the preprocessed microvessel images is shown in FIG. 2.

Morphological operations generally apply a structuring element to an input image, creating an output image of the same size. In a morphological operation, the value of each pixel in the output image is based on a comparison to the corresponding pixel in the input image with its neighbors. By choosing the size and shape of the neighborhood, a morphological operation that is sensitive to the specific shapes in the input image can be constructed.

In general, the morphological filtering implemented by the systems and methods described in the present disclosure includes converting the microvessel image (e.g., a preprocessed microvessel image output from a Hessian filter) to a binary image, as indicated at step 202; removing small noise-like objects through an erosion and dilation operation, as indicated at step 204; removing small holes, as indicated at step 206; filling small holes with a dilation and erosion operation, as indicated at step 208; generating an image skeleton, as indicated at step 210; cleaning the skeleton image, as indicated at step 212; removing spur pixels, as indicated at step 214; labeling connected components, as indicated at step 216; finding branch points, as indicated at step 218; dilating branch points, as indicated at step 220; removing branch points, as indicated at step 222; and removing small objects, as indicated at step 224. The output of this morphological filtering is an image that includes vessel segments, as indicated at step 226. These vessel segment data are subsequently analyzed to estimate desired quantitative parameters of the vessels. Although the steps of the morphological filtering are illustrated in a particular order in FIG. 2, in some embodiments one or more of the steps can be executed partially or entirely in parallel, can be executed in a different order than illustrated in FIG. 2, or can be bypassed.

In step 202, the microvessel image can be converted to a binary image by setting an intensity threshold. The output binary image, $I_B$ (x, z), replaces all pixel values in the input image with luminance greater than a selected threshold with values of 1, and replaces all other pixel values with values of 0. When the input image is an output of a Hessian filter and spectral subtraction, the input image will have values in the [0,1] range. In these instances, the threshold can be selected as a value in the same [0,1] range, which is the range output image after Hessian filtering.

In step 204, small noise-like objects can be removed from the binary image using erosion followed by dilation. Dilation adds pixels to the boundaries of objects in an image, while erosion removes pixels on object boundaries. The number of pixels added or removed from the objects in an image depends on the size and shape of the structuring element used to process the image. In the morphological dilation and erosion operations, the value of any given pixel in the output image is determined by applying a rule to the corresponding pixel and its neighbors in the input image.

In step 206, small holes are removed in the image output from step 204. Erroneous intensity nulling may exist in the input image at isolated points along the vessels with horizontal orientation. This intensity nulling is the effect of spectral nulling due to the ultrasound beam being perpendicular to the blood flow, resulting in symmetric spectrum in the frequency domain. Thus, the two components in the spectral subtraction of Eqn. (7) cancel each other. To avoid erroneous splitting of the vessels at these points, a morphological "hole-filling" is used to remove the small holes from the image output from step 204. As one example, removing the small holes can include setting a pixel to a value of 1 if five or more pixels in its 3-by-3 neighborhood are also 1 s; otherwise, the pixel value is set to 0. After this operation, some small holes may still remain. To remove the remaining small holes in the vessels, a dilation followed by erosion operation is used to fill the remaining holes, as indicated at step 208.

The next step in the morphological operations on the binary images is to generate a skeleton image by removing pixels on the boundaries of objects without allowing objects to break apart. For instance, generating a skeleton image can include removing pixels in the binary images so that an object without holes shrinks to a line, and so that an object with holes shrinks to a connected ring halfway between each hole and the outer boundary. As one example, the skeleton image can be generated using a thinning algorithm, such as the one described by L. Lam, et al., in "Thinning methodologies-a comprehensive survey," *IEEE Trans. on Pattern Analysis and Machine Intelligence*, 1992; 14:869-885, which is herein incorporated by reference in its entirety.

Figure 3:
FIGS. 3A-3D show an example of a thinning algorithm being applied to a binary image to iteratively skeletonize the binary image.

FIG. 3A shows an example of a binary vessel segment used as the input image of a thinning algorithm, and FIGS. 3B-3D show the output image of a thinning algorithm after 5, 10, and 20 iterations. By increasing the number of iterations, the output image of the thinning algorithm converges to a skeleton image.

In step 212, the skeleton image is cleaned up by removing isolated pixels (e.g., 1 s that are completely surrounded by 0 s), such as the center pixel in the following pattern, $$\begin{bmatrix} 0 & 0 & 0 \\ 0 & 1 & 0 \\ 0 & 0 & 0 \end{bmatrix}.$$

In step 214, spur pixels are removed from the skeleton image. Spurs can be removed using a morphological pruning algorithm. In general, the pruning algorithm will remove all branches shorter than a given number of points. If a spur is shorter than the given number of points the spur will be removed.

In step 216, connected components are labeled. For example, groups of pixels that include a selected number of connected pixels will be labeled as a separate component.

In step 218, branch points are found. For example, branch points can be found as follows:

$$I = \begin{bmatrix} 0 & 0 & 1 & 0 & 0 \\ 0 & 0 & 1 & 0 & 0 \\ 1 & 1 & 1 & 1 & 1 \\ 0 & 0 & 1 & 0 & 0 \\ 0 & 0 & 1 & 0 & 0 \end{bmatrix} \to I_B = \begin{bmatrix} 0 & 0 & 0 & 0 & 0 \\ 0 & 0 & 0 & 0 & 0 \\ 0 & 0 & 1 & 0 & 0 \\ 0 & 0 & 0 & 0 & 0 \\ 0 & 0 & 0 & 0 & 0 \end{bmatrix}.$$

In step 220, branch points are dilated. For example, branch points can be dilated using a disk structuring element with a dilating size of one pixel, as follows:

$$I_B = \begin{bmatrix} 0 & 0 & 0 & 0 & 0 \\ 0 & 0 & 0 & 0 & 0 \\ 0 & 0 & 1 & 0 & 0 \\ 0 & 0 & 0 & 0 & 0 \\ 0 & 0 & 0 & 0 & 0 \end{bmatrix} \to I_D = \begin{bmatrix} 0 & 0 & 0 & 0 & 0 \\ 0 & 0 & 1 & 0 & 0 \\ 0 & 1 & 1 & 1 & 0 \\ 0 & 0 & 1 & 0 & 0 \\ 0 & 0 & 0 & 0 & 0 \end{bmatrix}.$$

In step 222, branch points are removed from the skeleton image. For example, branch points can be removed using a disk dilated image with a dilating size of one pixel, as follows, $$I = \begin{bmatrix} 0 & 0 & 1 & 0 & 0 \\ 0 & 0 & 1 & 0 & 0 \\ 1 & 1 & 1 & 1 & 1 \\ 0 & 0 & 1 & 0 & 0 \\ 0 & 0 & 1 & 0 & 0 \end{bmatrix} \to I_B = \begin{bmatrix} 0 & 0 & 1 & 0 & 0 \\ 0 & 0 & 0 & 0 & 0 \\ 1 & 0 & 0 & 0 & 1 \\ 0 & 0 & 0 & 0 & 0 \\ 0 & 0 & 1 & 0 & 0 \end{bmatrix}.$$

In step 224, small objects (e.g., small vessels) are removed from the binary image. For example, vessels with a length less than a threshold length value can be removed from the binary image. Additionally or alternatively, vessels with a diameter less than a threshold diameter value can be removed from the binary image. The microvessel image is constructed from a sequence of two-dimensional ultrasound plane wave images in which some vessels are only partially visible in the imaging plane. This, in turn, results in observing small vessel segments in the image. The residual noise, when passed through the Hessian-based filtering, might also result in structures that may be perceived as small vessel segments. Hence, removing these unwanted, erroneous, or partial vessel segments can improve the reliability of the vessel segmentation.

Figure 4:
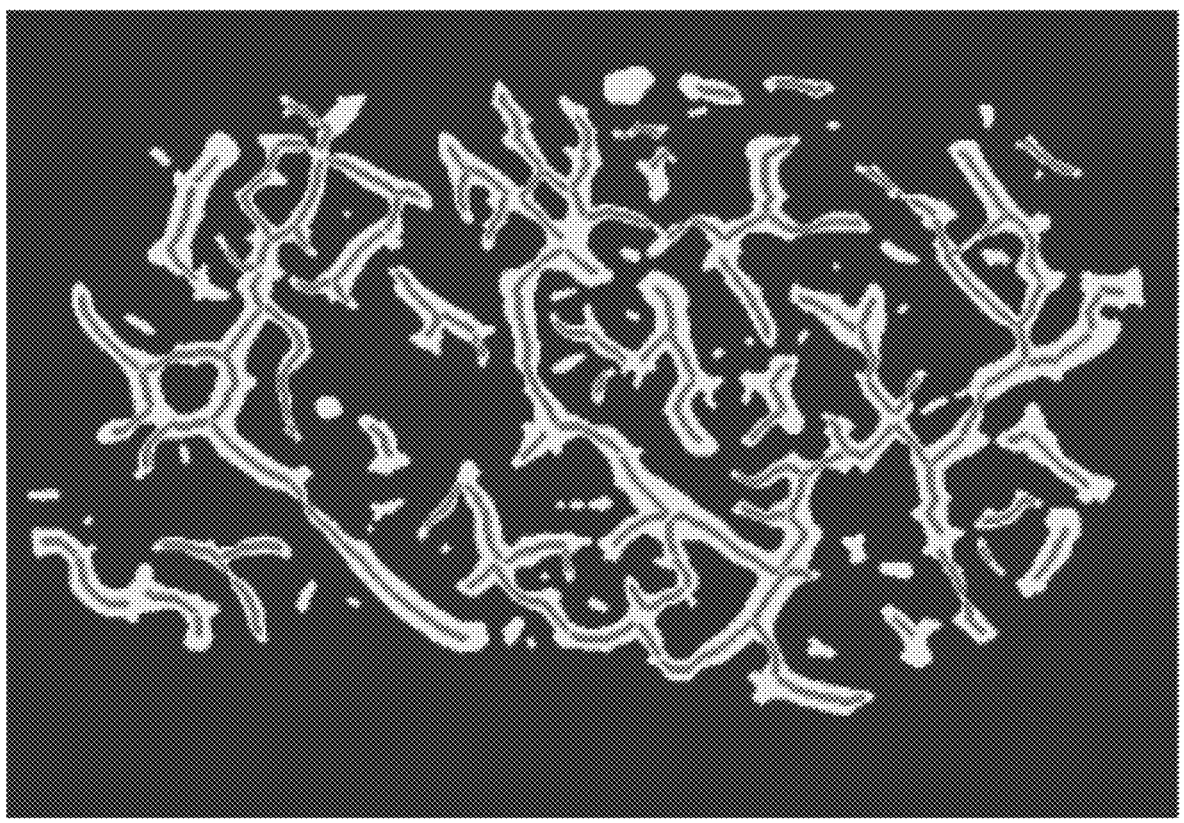
FIG. 4 is an example of vessel segment data displayed as being overlaid on a binary image generated from a microvessel image.

In step 226 the resulting vessel segment data are stored or output for additional processing. An example of vessel segment data is shown in FIG. 4. In this example, the vessel segment data are overlaid on a binary image of the microvessel image.

Referring again to FIG. 1, the vessel segment data output by performing morphological filtering on the input microvessel images are processed to quantify vessel feature data, as generally indicated at step 110. As one non-limiting example, the vessel feature data may include at least one of quantitative vessel structure data, quantitative spatial vascularity pattern data, quantitative fractal dimension data, quantitative vessel Murray's deviation data, quantitative bifurcation angle data, and quantitative closest vessel distance data.

The quantitative vessel feature data are then stored for later use, or displayed to a user, as indicated at step 112. For instance, the vessel feature data may be displayed in connection with a graphical user interface that enables a user to visualize the vessel feature data (e.g., as images, maps, or other display or textual elements), manipulate the vessel feature data, or otherwise interact with the vessel feature data.

Figure 5:
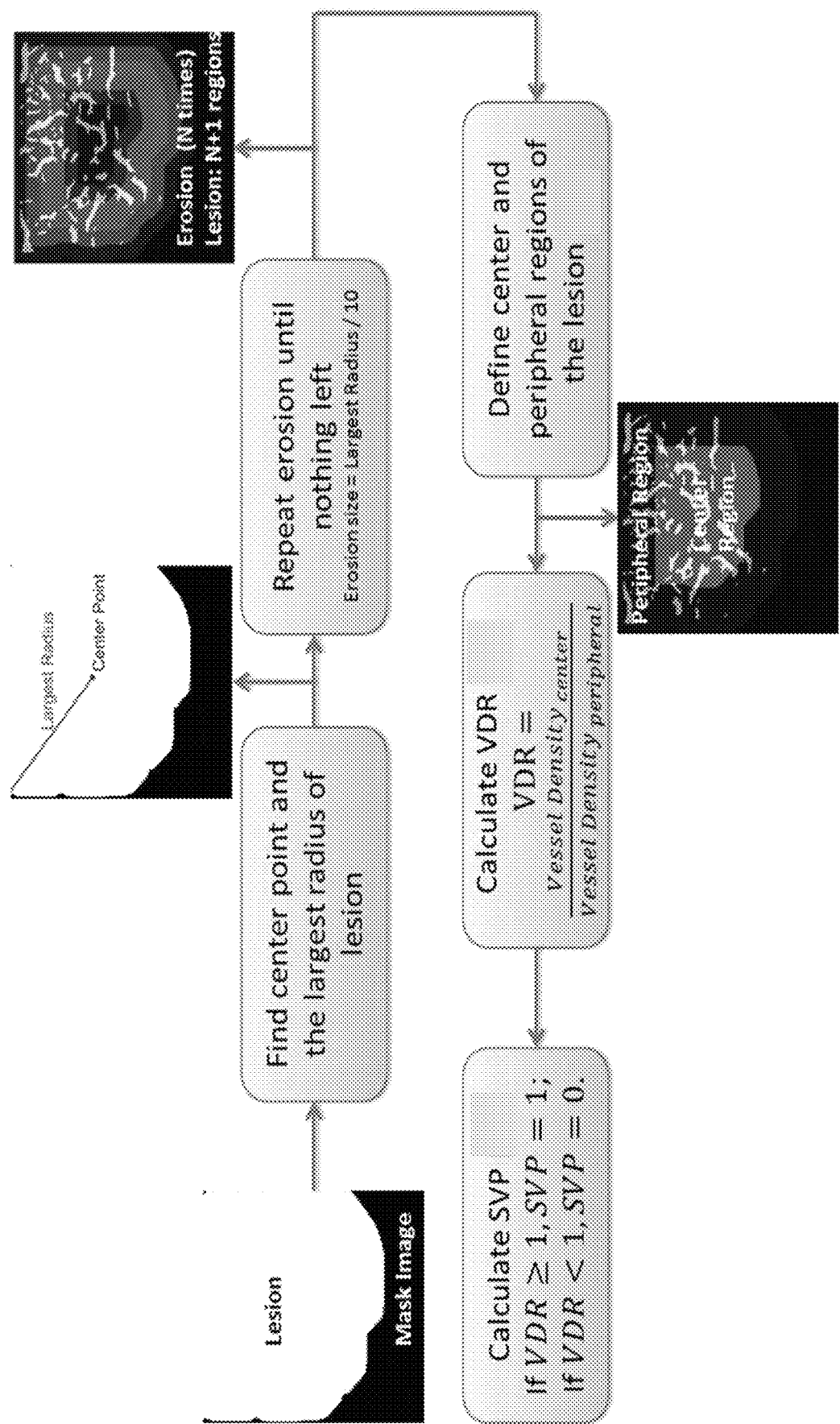
FIG. 5 shows an example workflow for generating spatial vascularity pattern ("SVP") data for a lesion, such as a breast cancer lesion, from ultrasound microvessel image data.

FIG. 5 shows an example workflow for estimating or otherwise computing spatial vascularity pattern data from ultrasound microvessel image data and binary image data generated therefrom.

The method includes generating segmented lesion data. The segmented lesion data generally indicate a binary mask corresponding to one or more segmented lesions. For example, the segmented lesion data can include a binary image having first binary values (e.g., non-zero values, such as 1) for pixels corresponding to or otherwise identified as being associated with a lesion, and second binary values (e.g., zero) for pixels not corresponding to a lesion. The segmented lesion data may be generated from the ultrasound image data from which the ultrasound microvessel images were generated, as an example. Additionally or alternatively, the segmented lesion data can be generated from other medical image data that are co-registered with the ultrasound microvessel image data.

The segmented lesion data are then used to define the center and peripheral regions of the lesion. For example, the center point and largest radius can first be determined for the segmented lesion. An image erosion operator can then be applied to the segmented lesion data with an erosion size defined based on the determined largest radius. For instance, the erosion size can be set as a percentage of the determined largest radius, such as 10 percent. The image erosion operator can then be repeated until all of the segmented lesion has been eroded. At each iteration, n, the eroded image for that iteration is stored. The number of iterations to completely erode the segmented lesion is N. The central region of the lesion can then be defined as the union of the first (N+1)/2 regions from the determined center point of the segmented lesion. The remaining regions are defined as the peripheral region. This iterative application of the image erosion to the segmented lesion data generate output as eroded lesion data, which can be used to define the central and peripheral regions of the segmented lesion.

Vessel density data are then computed based on the binary image data, which depict a binary representation of the microvessel network otherwise depicted in the ultrasound microvessel images. The vessel density data can include a vessel density ratio, which can be computed as:

$$VDR = \frac{\text{Vessel Density}_{center}}{\text{Vessel Density}_{peripheral}}$$

Thus, in some embodiments, the eroded lesion data can be used to mask the binary image data into central and peripheral regions, and a vessel density can be computed in each of those regions. The central region vessel density and the peripheral region vessel density are then used to compute the vessel density ratio.

Spatial vascularity pattern data are then generated based on the vessel density ratio. In general, the spatial vascularity pattern ("SVP") is defined as:

$VDR \geq 1, SVP=1$ $VDR < 1, SVP=0.$

The spatial vascularity pattern data can then be stored for later use and/or displayed to a user. For example, the spatial vascularity pattern data can be displayed to a user, such as via a graphical user interface. Additionally or alternatively, a report can be generated based on the spatial vascularity pattern data, as described above, and the report can be displayed to the user (e.g., via a graphical user interface or other display).

Figure 6:
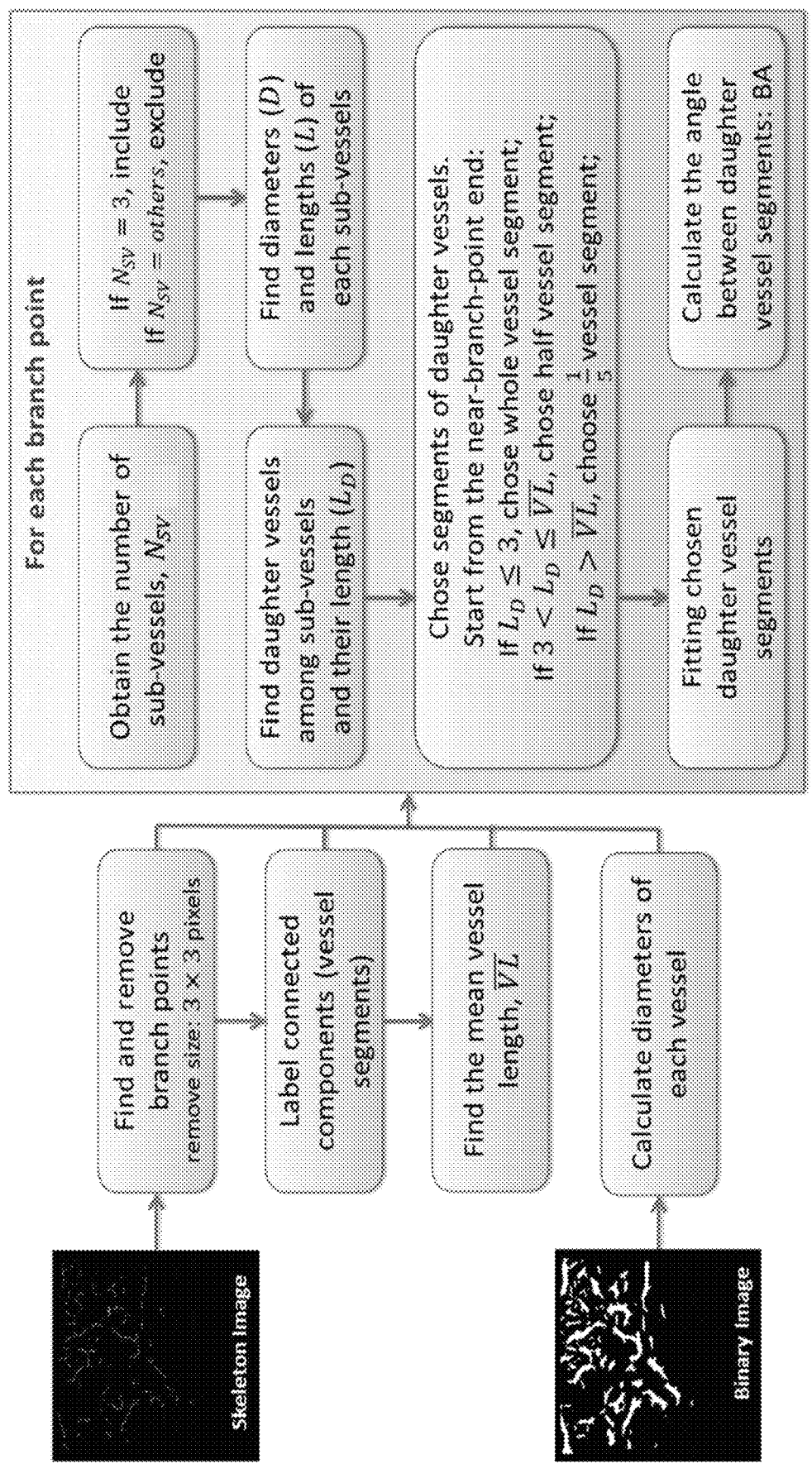
FIG. 6 shows an example workflow for generating bifurcation angle ("BA") data based on non-contrast ultrasound microvessel images.

FIG. 6 shows an example workflow for estimating or otherwise computing bifurcation angle data from ultrasound microvessel image data and binary image data generated therefrom. For example, bifurcation angle data may be computed using a skeleton image and binary image data, generated as described above.

The skeleton image is processed to remove all branch points to obtain separate vessel segments. For example, a 3×3 removal size can be used to remove the branch points. Vessel segment data are generated as a result, and each segment is assigned a unique label. The mean vessel length, $\overline{VL}$, is also calculated from the vessel segment data. The binary image and vessel segments locations are then used to calculate diameters of each vessel.

For each branch point, all sub-vessels and their diameters are found according to their label. The number of sub-vessels, $N_{SV}$, in a branch can be determined as the number of connected 1s within the binary image data within a neighborhood (e.g., a 4×4 pixel neighborhood) of a branch point. The branches with three sub-vessels are used for the bifurcation angle calculation. The diameters and lengths of each sub-vessel are calculated or otherwise determined. The sub-vessel with maximal diameter (mother vessel) is excluded and the other sub-vessels (daughter vessels) are selected. Segments of daughter vessels are chosen based on the following criteria, starting from the near-branch-point end:

If $L_D \leq 3$, chose the whole vessel segment

If $3 < L_D \leq \overline{VL}$, chose half of the vessel segment

If $L_D > \overline{VL}$, chose ⅕ the vessel segment

A fit (e.g., a polynomial fit) is then applied for each daughter vessel segment with one line and the angle between them is calculated as the bifurcation angle.

Figure 7:
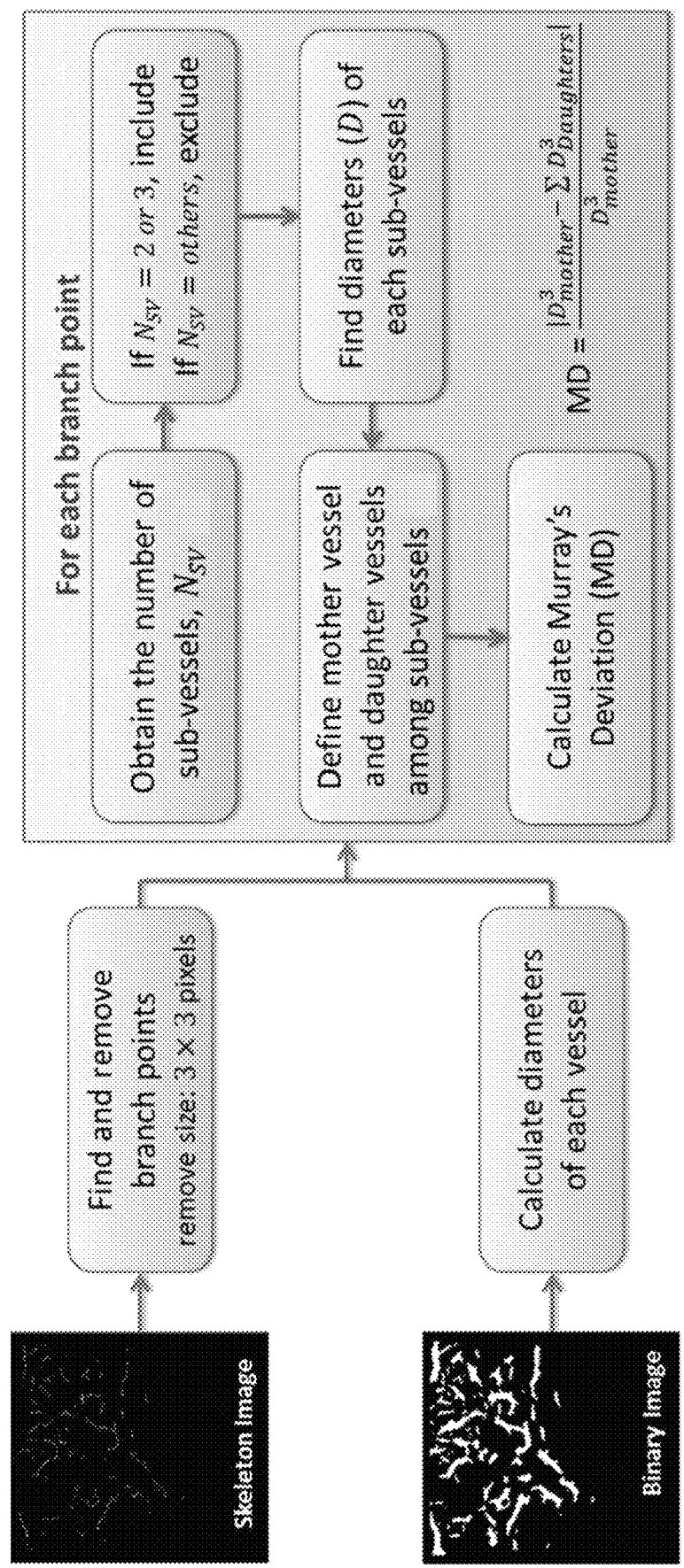
FIG. 7 shows an example workflow for generating Murray's deviation ("MD") data based on non-contrast ultrasound microvessel images.

FIG. 7 shows an example workflow for estimating or otherwise computing Murray's deviation data from ultrasound microvessel image data and binary image data generated therefrom. For example, Murray's deviation data may be computed using a skeleton image and binary image data, generated as described above.

Like the computation for bifurcation angle, the skeleton image is processed to remove all branch points to obtain separate vessel segments. For example, a 3×3 removal size can be used to remove the branch points. Vessel segment data are generated as a result, and each segment is assigned a unique label. The binary image and vessel segments locations are then used to calculate diameters of each vessel.

For each branch point, all sub-vessels and their diameters are found according to their label. The number of sub-vessels, $N_{SV}$, in a branch can be determined as the number of connected 1s within the binary image data within a neighborhood (e.g., a 4×4 pixel neighborhood) of a branch point. The branches with two or three sub-vessels are used for the Murray's deviation calculation. The diameters of each sub-vessel are calculated or otherwise determined. The sub-vessel with maximal diameter (mother vessel) is excluded and the other sub-vessels (daughter vessels) are selected. A Murray's deviation value is then computed based on the diameter of the mother ($D_{mother}$) and daughter ($D_{daughter}$) vessels as:

$$\frac{|D_{mother}^3 - \sum D_{Daughters}^3|}{D_{mother}^3}$$

Figure 8:
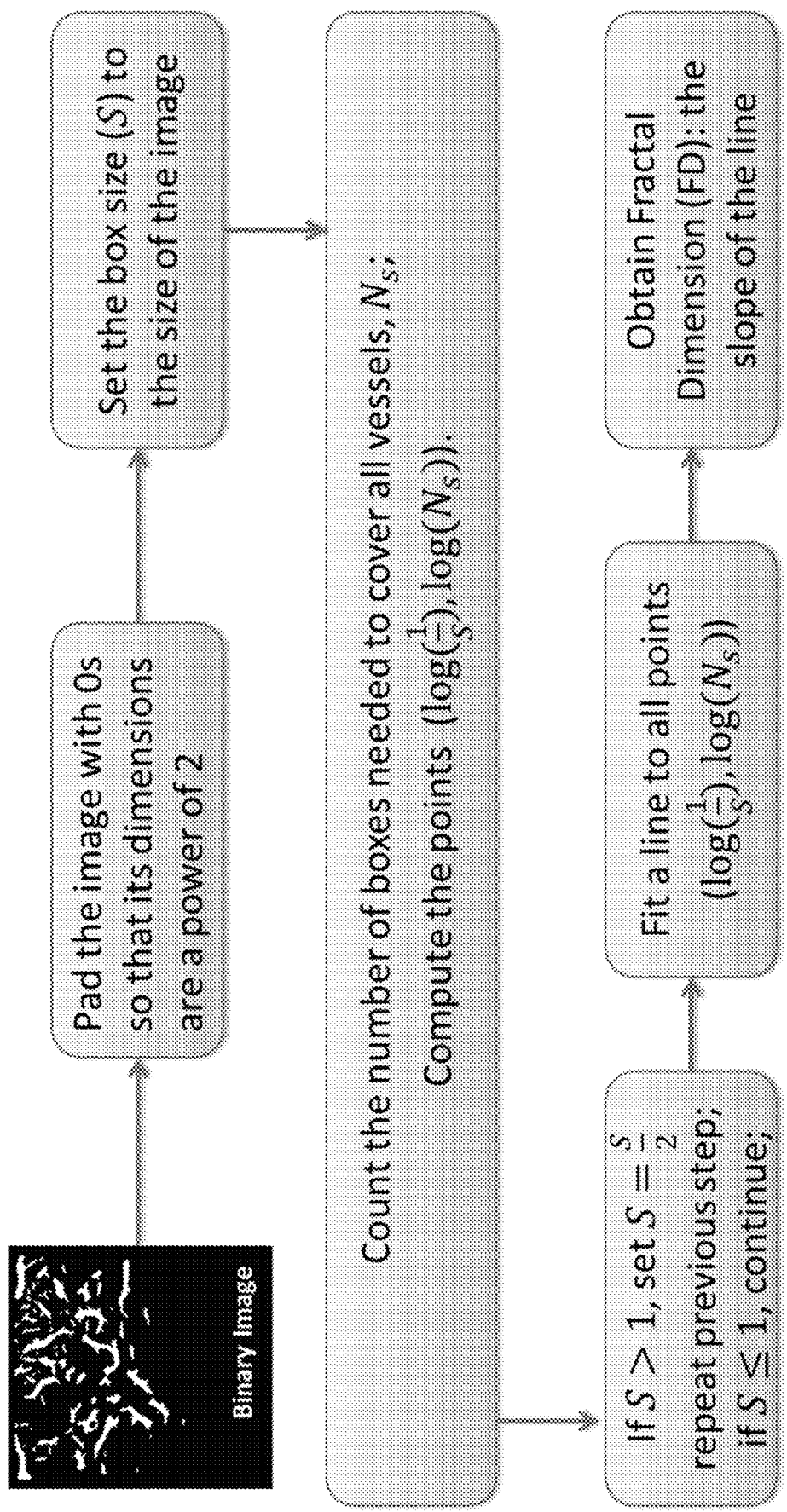
FIG. 8 shows an example workflow for generating fractal dimension ("FD") data based on non-contrast ultrasound microvessel images.

FIG. 8 shows an example workflow for estimating or otherwise computing fractal dimension data from ultrasound microvessel image data and binary image data generated therefrom. As an example, a box counting method can be used to calculate fractal dimension of the microvasculature structure using the binary image data as input. The binary image is padded with zeros until its dimensions are a power of two. If the dimensions of the binary image are already a power of two, then this step can be skipped in some instances.

The box size, S, is selected as the size of the binary image (after zero-padding if implemented). The box size is then decreased from the size of the after-padded binary image to 1. At each decrease step, k, the number, $N_S$, and size, S, of the boxes needed to cover all of the vessels are recorded, and the point, $P_k$=(log (1/S), log ($N_S$)), is calculated and stored. If, at a decrease step, S>1, then the value of the box size is set to S=S/2 and the previous step is repeated. When the box size is decreased to S=1, then the points, $p_k$, are fitted to a line and the slope is extracted as the fractal dimension.

Figure 9:
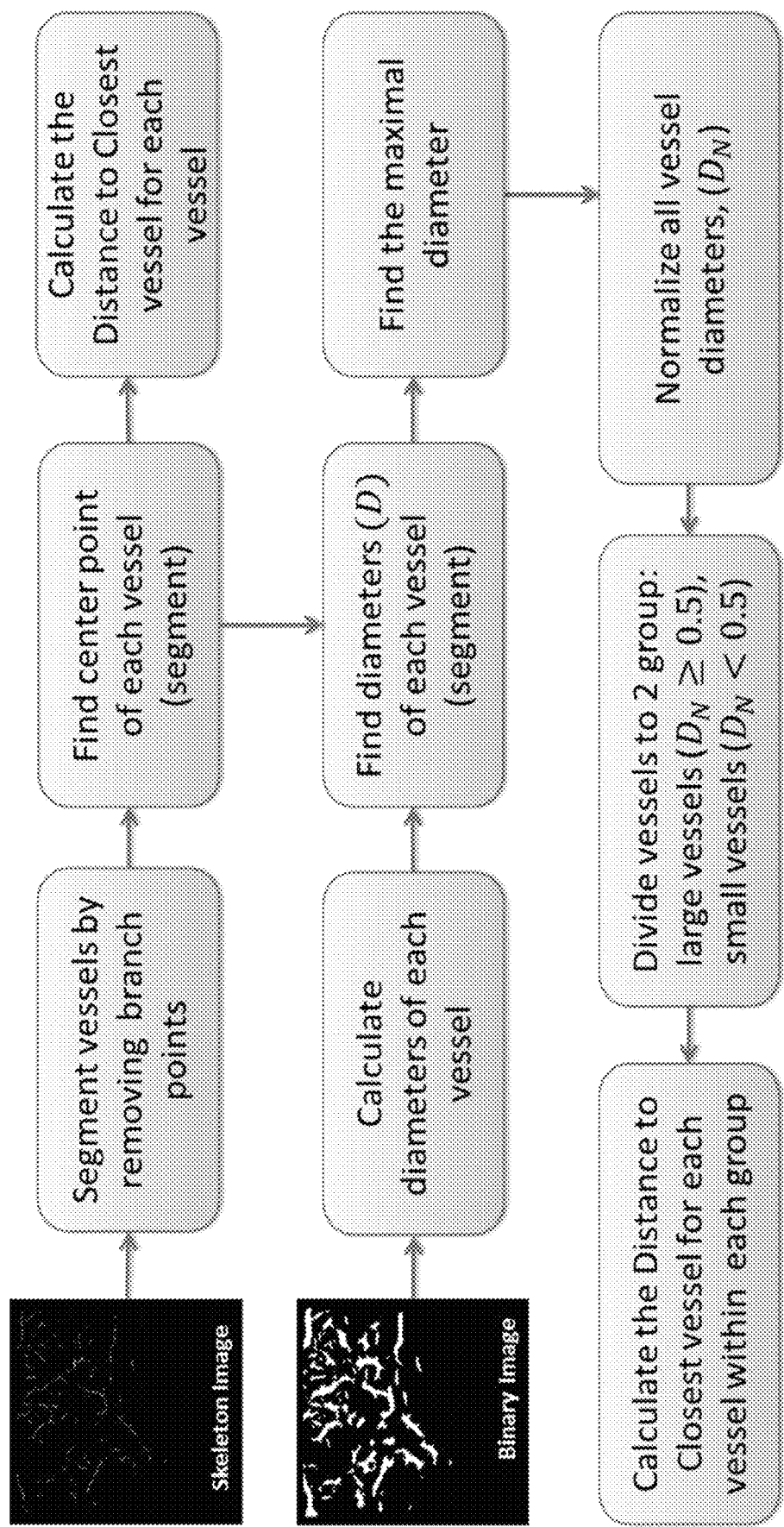
FIG. 9 shows an example workflow for generating closest distance parameter data based on non-contrast ultrasound microvessel images.

FIG. 9 shows an example workflow for estimating or otherwise computing closest distance parameter data from ultrasound microvessel image data and binary image data generated therefrom. For example, closest distance parameter data may be computed using a skeleton image and binary image data, generated as described above.

The skeleton image is processed to remove all branch points to obtain separate vessel segments. For example, a 3×3 removal size can be used to remove the branch points. Vessel segment data can be generated as a result, and each segment can be assigned a unique label. The location of the center point is found for each segment and the center points are stored as vessel segment center point data The binary image and the vessel segments are used to calculate the diameters, D, of each vessel. The maximal diameter is found and used to normalize the vessel diameters, $D_N$. Vessels are then divided into two groups according to their normalized vessel diameters $D_N$: a large vessel group containing vessels with a normalized diameter $D_N \geq 0.5$, and a small vessel group containing vessels with a normalized diameter $D_N < 0.5$. The closest distance between one vessel and its neighborhood vessels is then calculated within each group. In some embodiments, the closest distance parameter can be computed based on three groups of vessels: the group containing all vessels, the large vessel group, and the small vessel group.

Figure 10:
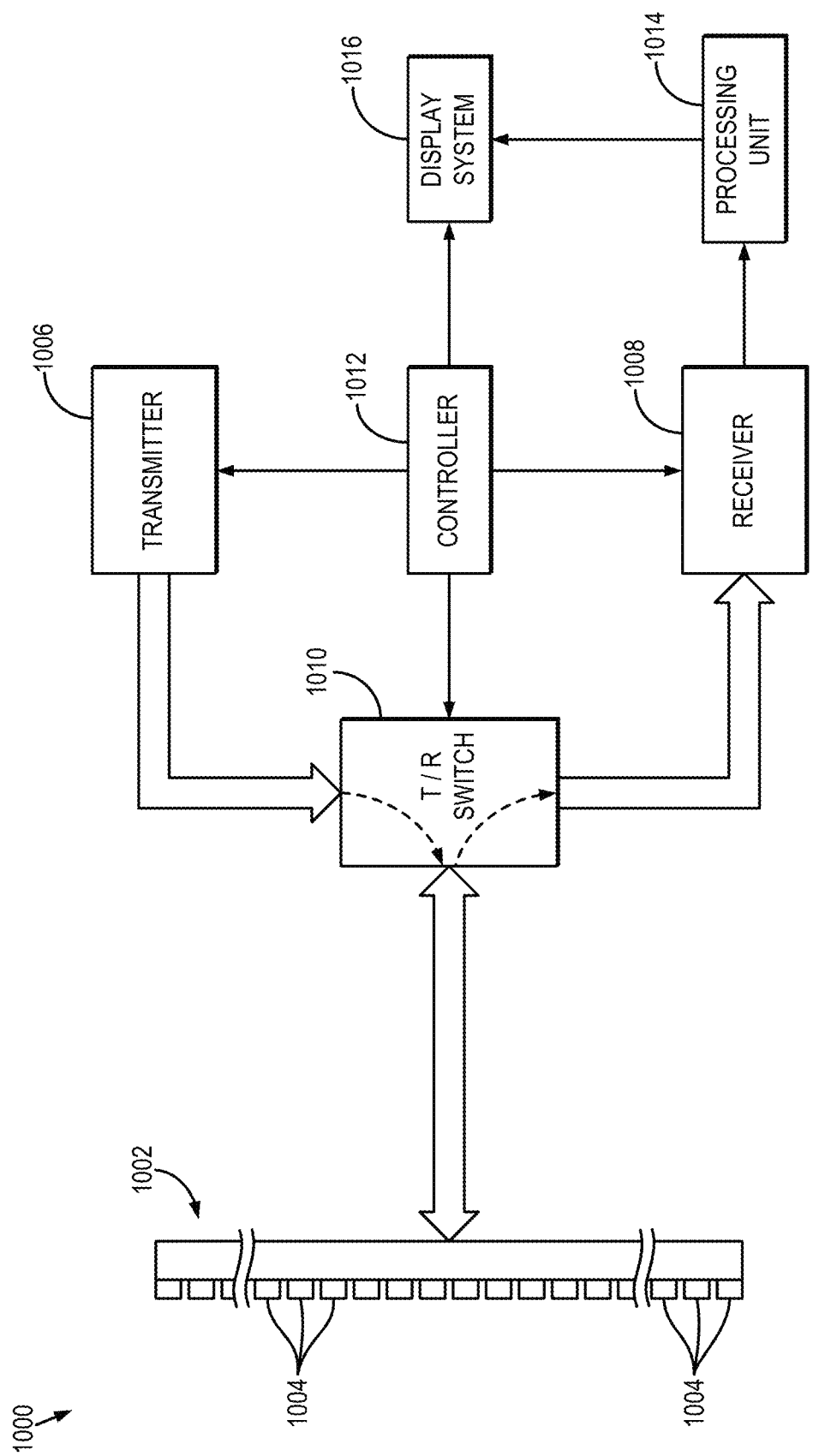
FIG. 10 is a block diagram of an example ultrasound system that can implement the methods described in the present disclosure.

FIG. 10 illustrates an example of an ultrasound system 1000 that can implement the methods described in the present disclosure. The ultrasound system 1000 includes a transducer array 1002 that includes a plurality of separately driven transducer elements 1004. The transducer array 1002 can include any suitable ultrasound transducer array, including linear arrays, curved arrays, phased arrays, and so on. Similarly, the transducer array 1002 can include a 1D transducer, a 1.5D transducer, a 1.75D transducer, a 2D transducer, a 3D transducer, and so on.

When energized by a transmitter 1006, a given transducer element 1004 produces a burst of ultrasonic energy. The ultrasonic energy reflected back to the transducer array 1002 (e.g., an echo) from the object or subject under study is converted to an electrical signal (e.g., an echo signal) by each transducer element 1004 and can be applied separately to a receiver 1008 through a set of switches 1010. The transmitter 1006, receiver 1008, and switches 1010 are operated under the control of a controller 1012, which may include one or more processors. As one example, the controller 1012 can include a computer system.

The transmitter 1006 can be programmed to transmit unfocused or focused ultrasound waves. In some configurations, the transmitter 1006 can also be programmed to transmit diverged waves, spherical waves, cylindrical waves, plane waves, or combinations thereof. Furthermore, the transmitter 1006 can be programmed to transmit spatially or temporally encoded pulses.

The receiver 1008 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 1006 and the receiver 1008 can be programmed to implement a high frame rate. For instance, a frame rate associated with an acquisition pulse repetition frequency ("PRF") of at least 100 Hz can be implemented. In some configurations, the ultrasound system 1000 can sample and store at least one hundred ensembles of echo signals in the temporal direction.

A scan can be performed by setting the switches 1010 to their transmit position, thereby directing the transmitter 1006 to be turned on momentarily to energize transducer elements 1004 during a single transmission event. The switches 1010 can then be set to their receive position and the subsequent echo signals produced by the transducer elements 1004 in response to one or more detected echoes are measured and applied to the receiver 1008. The separate echo signals from the transducer elements 1004 can be combined in the receiver 1008 to produce a single echo signal.

The echo signals are communicated to a processing unit 1014, which may be implemented by a hardware processor and memory, to process echo signals or images generated from echo signals. As an example, the processing unit 1014 can implement the methods described in the present disclosure for generating quantitative vessel feature data from non-contrast ultrasound data. Images produced from the echo signals by the processing unit 1014 can be displayed on a display system 1016.

Figure 11:
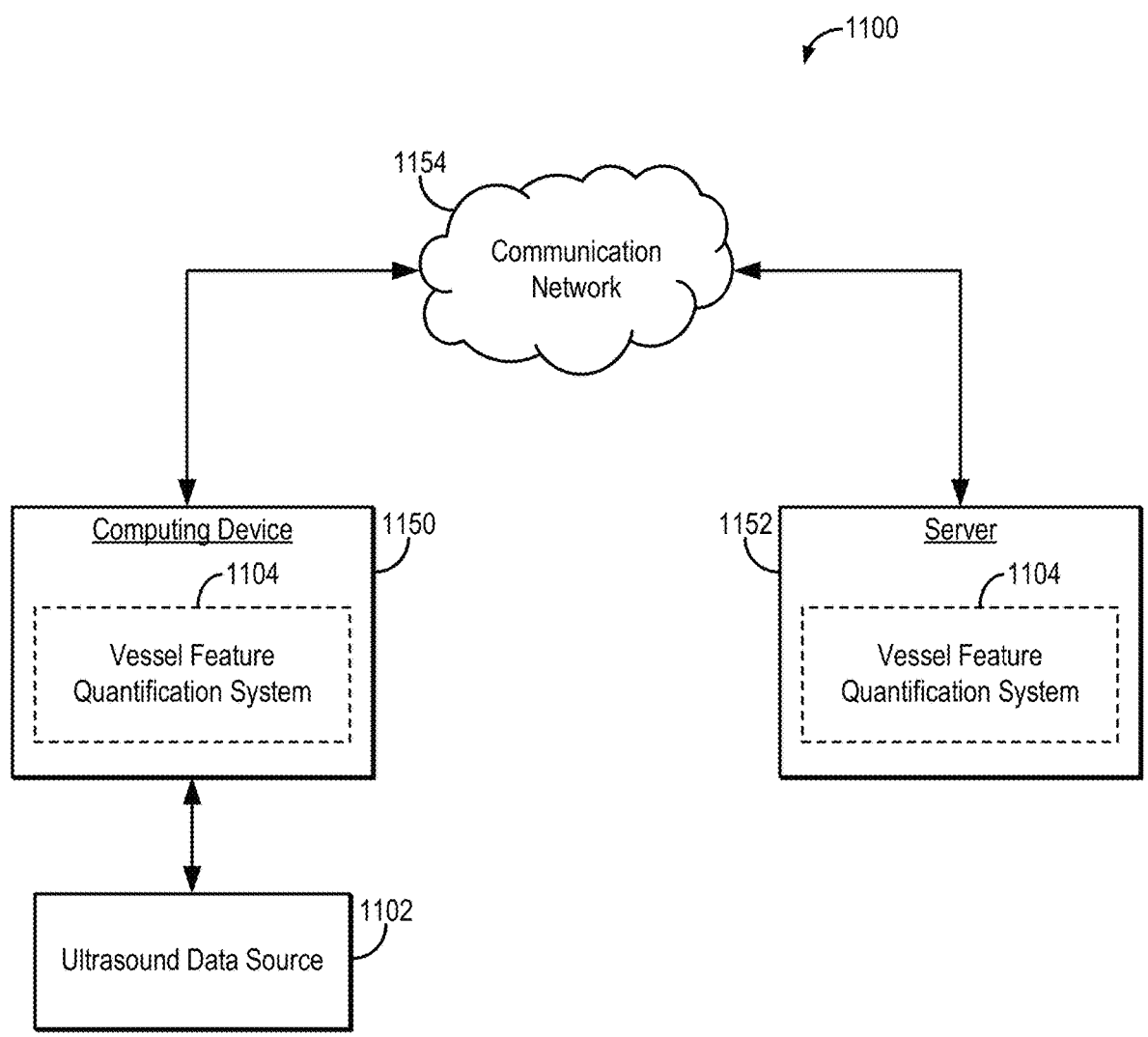
FIG. 11 is a block diagram of an example system for quantifying vessel feature data from non-contrast ultrasound images of tissue microvasculature.

Referring now to FIG. 11, an example of a system 1100 for quantifying vessel feature data from non-contrast ultrasound data in accordance with some embodiments of the systems and methods described in the present disclosure is shown. As shown in FIG. 11, a computing device 1150 can receive one or more types of data (e.g., non-contrast ultrasound data, microvessel images) from ultrasound data source 1102, which may be an ultrasound data source. In some embodiments, computing device 1150 can execute at least a portion of a vessel feature quantification system 1104 to generate quantitative vessel feature data from data received from the ultrasound data source 1102.

Additionally or alternatively, in some embodiments, the computing device 1150 can communicate information about data received from the ultrasound data source 1102 to a server 1152 over a communication network 1154, which can execute at least a portion of the vessel feature quantification system 1104 to generate quantitative vessel feature data from data received from the ultrasound data source 1102. In such embodiments, the server 1152 can return information to the computing device 1150 (and/or any other suitable computing device) indicative of an output of the vessel feature quantification system 1104 to generate quantitative vessel feature data from data received from the ultrasound data source 1102.

In some embodiments, computing device 1150 and/or server 1152 can be any suitable computing device or combination of devices, such as a desktop computer, a laptop computer, a smartphone, a tablet computer, a wearable computer, a server computer, a virtual machine being executed by a physical computing device, and so on. The computing device 1150 and/or server 1152 can also reconstruct images from the data.

In some embodiments, ultrasound data source 1102 can be any suitable source of image data (e.g., measurement data, images reconstructed from measurement data), such as an ultrasound system, another computing device (e.g., a server storing image data), and so on. In some embodiments, ultrasound data source 1102 can be local to computing device 1150. For example, ultrasound data source 1102 can be incorporated with computing device 1150 (e.g., computing device 1150 can be configured as part of a device for capturing, scanning, and/or storing images). As another example, ultrasound data source 1102 can be connected to computing device 1150 by a cable, a direct wireless link, and so on. Additionally or alternatively, in some embodiments, ultrasound data source 1102 can be located locally and/or remotely from computing device 1150, and can communicate data to computing device 1150 (and/or server 1152) via a communication network (e.g., communication network 1154).

In some embodiments, communication network 1154 can be any suitable communication network or combination of communication networks. For example, communication network 1154 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 108 can be a local area network, a wide area network, a public network (e.g., the Internet), a private or semi-private network (e.g., a corporate or university intranet), any other suitable type of network, or any suitable combination of networks. Communications links shown in FIG. 11 can each be any suitable communications link or combination of communications links, such as wired links, fiber optic links, Wi-Fi links, Bluetooth links, cellular links, and so on.

Figure 12:
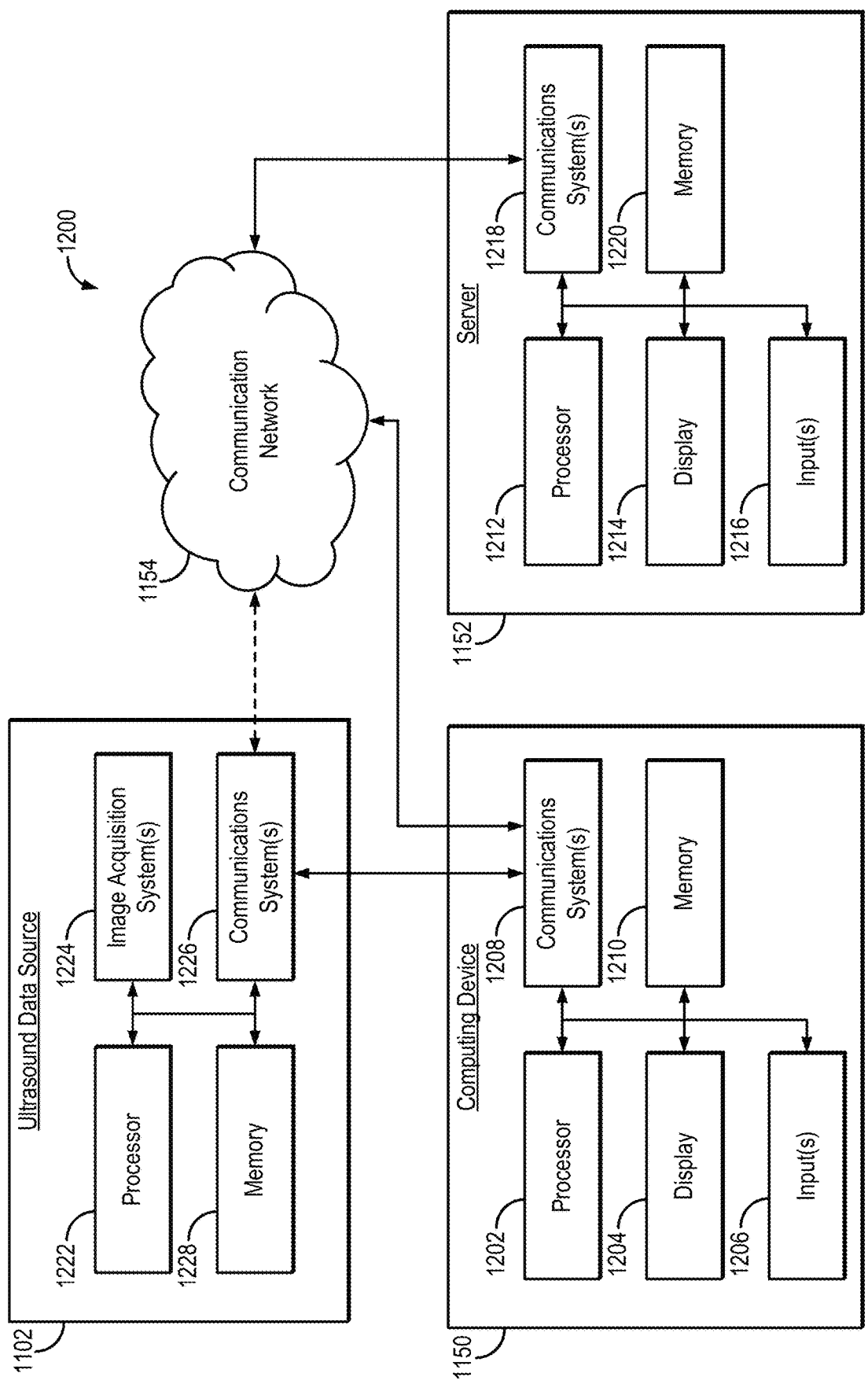
FIG. 12 is a block diagram of example hardware that can implement the system of FIG. 11.

Referring now to FIG. 12, an example of hardware 1200 that can be used to implement ultrasound data source 1102, computing device 1150, and server 1154 in accordance with some embodiments of the systems and methods described in the present disclosure is shown. As shown in FIG. 12, in some embodiments, computing device 1150 can include a processor 1202, a display 1204, one or more inputs 1206, one or more communication systems 1208, and/or memory 1210. In some embodiments, processor 1202 can be any suitable hardware processor or combination of processors, such as a central processing unit ("CPU"), a graphics processing unit ("GPU"), and so on. In some embodiments, display 1204 can include any suitable display devices, such as a computer monitor, a touchscreen, a television, and so on. In some embodiments, inputs 1206 can include any suitable input devices and/or sensors that can be used to receive user input, such as a keyboard, a mouse, a touchscreen, a microphone, and so on.

In some embodiments, communications systems 1208 can include any suitable hardware, firmware, and/or software for communicating information over communication network 1154 and/or any other suitable communication networks. For example, communications systems 1208 can include one or more transceivers, one or more communication chips and/or chip sets, and so on. In a more particular example, communications systems 1208 can include hardware, firmware and/or software that can be used to establish a Wi-Fi connection, a Bluetooth connection, a cellular connection, an Ethernet connection, and so on.

In some embodiments, memory 1210 can include any suitable storage device or devices that can be used to store instructions, values, data, or the like, that can be used, for example, by processor 1202 to present content using display 1204, to communicate with server 1152 via communications system(s) 1208, and so on. Memory 1210 can include any suitable volatile memory, non-volatile memory, storage, or any suitable combination thereof. For example, memory 1210 can include RAM, ROM, EEPROM, one or more flash drives, one or more hard disks, one or more solid state drives, one or more optical drives, and so on. In some embodiments, memory 1210 can have encoded thereon, or otherwise stored therein, a computer program for controlling operation of computing device 1150. In such embodiments, processor 1202 can execute at least a portion of the computer program to present content (e.g., images, user interfaces, graphics, tables), receive content from server 1152, transmit information to server 1152, and so on.

In some embodiments, server 1152 can include a processor 1212, a display 1214, one or more inputs 1216, one or more communications systems 1218, and/or memory 1220. In some embodiments, processor 1212 can be any suitable hardware processor or combination of processors, such as a CPU, a GPU, and so on. In some embodiments, display 1214 can include any suitable display devices, such as a computer monitor, a touchscreen, a television, and so on. In some embodiments, inputs 1216 can include any suitable input devices and/or sensors that can be used to receive user input, such as a keyboard, a mouse, a touchscreen, a microphone, and so on.

In some embodiments, communications systems 1218 can include any suitable hardware, firmware, and/or software for communicating information over communication network 1154 and/or any other suitable communication networks. For example, communications systems 1218 can include one or more transceivers, one or more communication chips and/or chip sets, and so on. In a more particular example, communications systems 1218 can include hardware, firmware and/or software that can be used to establish a Wi-Fi connection, a Bluetooth connection, a cellular connection, an Ethernet connection, and so on.

In some embodiments, memory 1220 can include any suitable storage device or devices that can be used to store instructions, values, data, or the like, that can be used, for example, by processor 1212 to present content using display 1214, to communicate with one or more computing devices 1150, and so on. Memory 1220 can include any suitable volatile memory, non-volatile memory, storage, or any suitable combination thereof. For example, memory 1220 can include RAM, ROM, EEPROM, one or more flash drives, one or more hard disks, one or more solid state drives, one or more optical drives, and so on. In some embodiments, memory 1220 can have encoded thereon a server program for controlling operation of server 1152. In such embodiments, processor 1212 can execute at least a portion of the server program to transmit information and/or content (e.g., data, images, a user interface) to one or more computing devices 1150, receive information and/or content from one or more computing devices 1150, receive instructions from one or more devices (e.g., a personal computer, a laptop computer, a tablet computer, a smartphone), and so on.

In some embodiments, ultrasound data source 1102 can include a processor 1222, one or more image acquisition systems 1224, one or more communications systems 1226, and/or memory 1228. In some embodiments, processor 1222 can be any suitable hardware processor or combination of processors, such as a CPU, a GPU, and so on. In some embodiments, the one or more image acquisition systems 1224 are generally configured to acquire data, images, or both, and can include an ultrasound transducer. Additionally or alternatively, in some embodiments, one or more image acquisition systems 1224 can include any suitable hardware, firmware, and/or software for coupling to and/or controlling operations of an ultrasound transducer. In some embodiments, one or more portions of the one or more image acquisition systems 1224 can be removable and/or replaceable.

Note that, although not shown, ultrasound data source 1102 can include any suitable inputs and/or outputs. For example, ultrasound data source 1102 can include input devices and/or sensors that can be used to receive user input, such as a keyboard, a mouse, a touchscreen, a microphone, a trackpad, a trackball, and so on. As another example, ultrasound data source 1102 can include any suitable display devices, such as a computer monitor, a touchscreen, a television, etc., one or more speakers, and so on.

In some embodiments, communications systems 1226 can include any suitable hardware, firmware, and/or software for communicating information to computing device 1150 (and, in some embodiments, over communication network 1154 and/or any other suitable communication networks). For example, communications systems 1226 can include one or more transceivers, one or more communication chips and/or chip sets, and so on. In a more particular example, communications systems 1226 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1228 can include any suitable storage device or devices that can be used to store instructions, values, data, or the like, that can be used, for example, by processor 1222 to control the one or more image acquisition systems 1224, and/or receive data from the one or more image acquisition systems 1224; to images from data; present content (e.g., images, a user interface) using a display; communicate with one or more computing devices 1150; and so on. Memory 1228 can include any suitable volatile memory, non-volatile memory, storage, or any suitable combination thereof. For example, memory 1228 can include RAM, ROM, EEPROM, one or more flash drives, one or more hard disks, one or more solid state drives, one or more optical drives, and so on. In some embodiments, memory 1228 can have encoded thereon, or otherwise stored therein, a program for controlling operation of ultrasound data source 1102. In such embodiments, processor 1222 can execute at least a portion of the program to generate images, transmit information and/or content (e.g., data, images) to one or more computing devices 1150, receive information and/or content from one or more computing devices 1150, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating quantitative vessel feature data from non-contrast ultrasound data, the steps of the method comprising:
    (a) providing a microvessel image to a computer system, the microvessel image having been acquired with an ultrasound system from a subject without a contrast agent;
    (b) converting the microvessel image to a binary image using the computer system, wherein the binary image contains pixels with first binary values and pixels with second binary values, wherein pixels with the first binary value correspond to segmented vessels;
    (c) generating vessel segment data from the binary image by morphologically filtering the binary image using the computer system, wherein the vessel segment data represent segmented vessels depicted in the microvessel image;
    (d) generating quantitative vessel feature data based on at least one of the binary image and the vessel segment data, the quantitative vessel feature data comprising at least one of quantitative vessel structure data, quantitative vessel Murray's deviation data, quantitative bifurcation angle data, quantitative closest vessel distance data, quantitative fractal dimension data, and quantitative spatial vascularity pattern data; and
    (e) displaying the quantitative vessel feature data to a user.

2. The method of claim 1, wherein the quantitative vessel feature data comprise vessel structure data indicative of at least one of a number of vessels depicted in the microvessel image, a Murray's deviation of vessels depicted in the microvessel image, a bifurcation angle of vessels depicted in the microvessel image, a closest vessel distance depicted in the microvessel image, a spatial vascularity pattern depicted in the microvessel image, or combinations thereof.

3. The method of claim 1, wherein the morphological filtering comprises a thinning algorithm applied to the binary image, generating output as a skeletonized binary image from which the quantitative vessel feature data are generated in step (d).

4. The method of claim 3, wherein the skeletonized binary image is further processed to find and label branch points in the skeletonized binary image.

5. The method of claim 4, wherein the skeletonized binary image is further processed to remove each branch point to define vessels and sub-vessels.

6. The method of claim 5, wherein the skeletonized binary image is further processed to calculate a vessel diameter at each pixel in the vessel segment data corresponding to one of the sub-vessels.

7. The method of claim 6, wherein the vessel diameter at a pixel is determined by:
computing a distance between that pixel and a nearest non-vessel pixel in the vessel segment data of the binary image;
assigning twice the distance to the pixel as a vessel diameter value for that pixel.

8. The method of claim 6, wherein the skeletonized binary image is further processed to label a sub-vessel with maximal diameter as a mother sub-vessel and to label each other sub-vessel as a daughter sub-vessel.

9. The method of claim 8, wherein the quantitative vessel feature data comprise vessel Murray's deviation data, and wherein the vessel Murray's deviation data are generated by computing a ratio between sub-vessel diameter data for the mother sub-vessel and each daughter sub-vessel using Murray's law.

10. The method of claim 8, wherein quantitative vessel feature data comprise vessel bifurcation angle data for each vessel segment by labeling the sub-vessels for that vessel segment and calculating the angle between daughter sub-vessels.

11. The method of claim 10, wherein the angle between the daughter sub-vessels is computed using an adaptive fit.

12. The method of claim 1, wherein the quantitative vessel feature data comprise vessel spatial vascularity pattern data indicating a distribution of vessel density within a central region of a region-of-interest relative to vessel density in a peripheral region of the region-of-interest.

13. The method of claim 12, wherein the region-of-interest corresponds to a lesion.

14. The method of claim 12, wherein the quantitative vessel spatial vascularity pattern is calculated by:
determining a center point and largest radius of the region-of-interest;
iteratively applying an image erosion operator to a binary mask corresponding to the region-of-interest, generating an eroded binary image at each iteration; and
defining the central region and the peripheral region based on the eroded binary image from each iteration.

15. The method of claim 14, wherein the central region is defined as a union of (N+1)/2 eroded binary images determined from the center point of the region-of-interest, wherein N is a total number of iterations of the image erosion operator.

16. The method of claim 12, further comprising calculating a vessel density ratio (VDR) as a ratio of vessel density in the central region to vessel density in the peripheral region.

17. The method of claim 16, wherein the vessel spatial vascularity pattern data have a value of one for values of VDR greater than or equal to one, and have a value of zero for values of VDR less than one.

18. The method of claim 17, wherein the region-of-interest corresponds to a lesion and the lesion is classified as having perilesional vascularization for vessel spatial vascularity pattern data equal to zero and classified as having intralesional vascularization for vessel spatial vascularity pattern data equal to one.

19. The method of claim 1, wherein the quantitative vessel feature data comprise vessel fractal dimension data indicating a repeating structure of vessel across a range of scales of vasculature viewed as a fractal.

20. The method of claim 19, wherein the vessel fractal dimension data are calculated using a box counting method.

21. The method of claim 1, wherein the quantitative vessel feature data comprise closest vessel distance data indicating a distance to a closest vessel for each vessel.

22. The method of claim 21, wherein the closest vessel distance data are processed to define a large vessel group based on vessels having a diameter at or above a threshold value, and a small vessel group based on vessels having a diameter below the threshold value.

23. The method of claim 22, wherein the closest vessel distance is calculated to a closest vessel for each vessel within each of the large vessel group and the small vessel group.

24. The method of claim 1, wherein the quantitative vessel feature data are analyzed using the computer system to classify a disease type in a body organ including at least one of a breast, a thyroid, and a lymph node.

25. The method of claim 1, wherein the quantitative vessel feature data are analyzed using the computer system to stage a disease progression in a tissue from which the ultrasound microvessel image was acquired.

26. The method of claim 1, wherein the quantitative vessel feature data are analyzed using the computer system to monitor a treatment response to a treatment provided to a tissue from which the ultrasound microvessel image was acquired.

* * * * *

UNITED STATES PATENT AND TRADEMARK OFFICE
CERTIFICATE OF CORRECTION

PATENT NO. : 12,175,662 B2
APPLICATION NO. : 17/466773
DATED : December 24, 2024
INVENTOR(S) : Azra Alizad et al.

It is certified that error appears in the above-identified patent and that said Letters Patent is hereby corrected as shown below:

In the Specification

Column 4, Line 55, "$(n_x n_z) \times n_t$" should be --$(n_x \times n_z) \times n_t$--.

Column 4, Eq (2), "$S_C = U \Delta V^\backslash$" should be --$S_C = U \Delta V \dagger$--.

Column 4, Line 61, "$n_i \times n_t$" should be --$n_t \times n_t$--.

Column 4, Line 61, "$\backslash$" should be --$\dagger$--.

Column 5, Line 8, "$n_i$" should be --$n_t$--.

Column 11, Line 29, "$P_k$" should be --$p_k$--.

Signed and Sealed this
Twenty-fifth Day of February, 2025

Coke Morgan Stewart
*Acting Director of the United States Patent and Trademark Office*